US009482628B2

(12) United States Patent
Naito et al.

(10) Patent No.: US 9,482,628 B2
(45) Date of Patent: Nov. 1, 2016

(54) IMAGING APPARATUS, CONTROL METHOD THEREFOR, AND STORAGE MEDIUM

(71) Applicant: CANON KABUSHIKI KAISHA, Tokyo (JP)

(72) Inventors: Yuichi Naito, Yokohama (JP); Kanako Dowaki, Tokyo (JP); Kazumasa Matsumoto, Yokohama (JP); Takashi Yamazaki, Asaka (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 58 days.

(21) Appl. No.: 13/945,068

(22) Filed: Jul. 18, 2013

(65) Prior Publication Data

US 2014/0037056 A1 Feb. 6, 2014

(30) Foreign Application Priority Data

Jul. 31, 2012 (JP) .................................. 2012-170378

(51) Int. Cl.
| G01N 23/04 | (2006.01) |
| H04N 5/32 | (2006.01) |
| A61B 6/00 | (2006.01) |
| H04N 5/361 | (2011.01) |
| H04N 5/363 | (2011.01) |
| H04N 5/365 | (2011.01) |

(52) U.S. Cl.
CPC ............. *G01N 23/04* (2013.01); *A61B 6/5258* (2013.01); *H04N 5/32* (2013.01); *H04N 5/361* (2013.01); *H04N 5/363* (2013.01); *H04N 5/3655* (2013.01)

(58) Field of Classification Search
CPC ........ G01N 23/04; H04N 5/32; H04N 5/361; H04N 5/363; H04N 5/3655; A61B 6/5258

USPC ........ 378/62, 91, 98, 98.8, 98.12, 207, 210; 250/370.09; 348/241, 294, 300, 308, 348/372; 382/132

See application file for complete search history.

(56) References Cited

U.S. PATENT DOCUMENTS

| 4,366,382 A * | 12/1982 | Kotowski ....................... 378/57 |
| 6,453,008 B1 * | 9/2002 | Sakaguchi et al. .......... 378/98.7 |
| 8,475,043 B2 | 7/2013 | Matsumoto ................... 378/205 |
| 2008/0136743 A1 | 6/2008 | Okada ............................ 345/55 |
| 2011/0121191 A1 * | 5/2011 | Kappler .................... G01T 1/17 250/370.09 |
| 2011/0127441 A1 * | 6/2011 | Tanabe ..................... 250/370.08 |
| 2014/0036118 A1 | 2/2014 | Dowaki et al. ............... 348/294 |

FOREIGN PATENT DOCUMENTS

| JP | A 2002-026302 | 1/2002 |
| JP | A 2002-344809 | 11/2002 |
| JP | A 2002-345797 | 12/2002 |

* cited by examiner

*Primary Examiner* — Thomas R Artman
(74) *Attorney, Agent, or Firm* — Fitzpatrick, Cella, Harper & Scinto

(57) ABSTRACT

An imaging apparatus determines, based on a frame interval associated with imaging of the object, the number of output values to be measured, and inputs electric signals of a given value to amplifiers to measure the determined number of output values during a time after a readout circuit performs a readout operation for the photoelectric conversion elements of one line and before the readout circuit performs a readout operation for the photoelectric conversion elements of the next one line, calculates a difference between the measured output value and a predetermined reference value, and corrects a measurement value of one line of the object by increasing or decreasing the measurement value by the difference.

30 Claims, 11 Drawing Sheets

F I G. 8
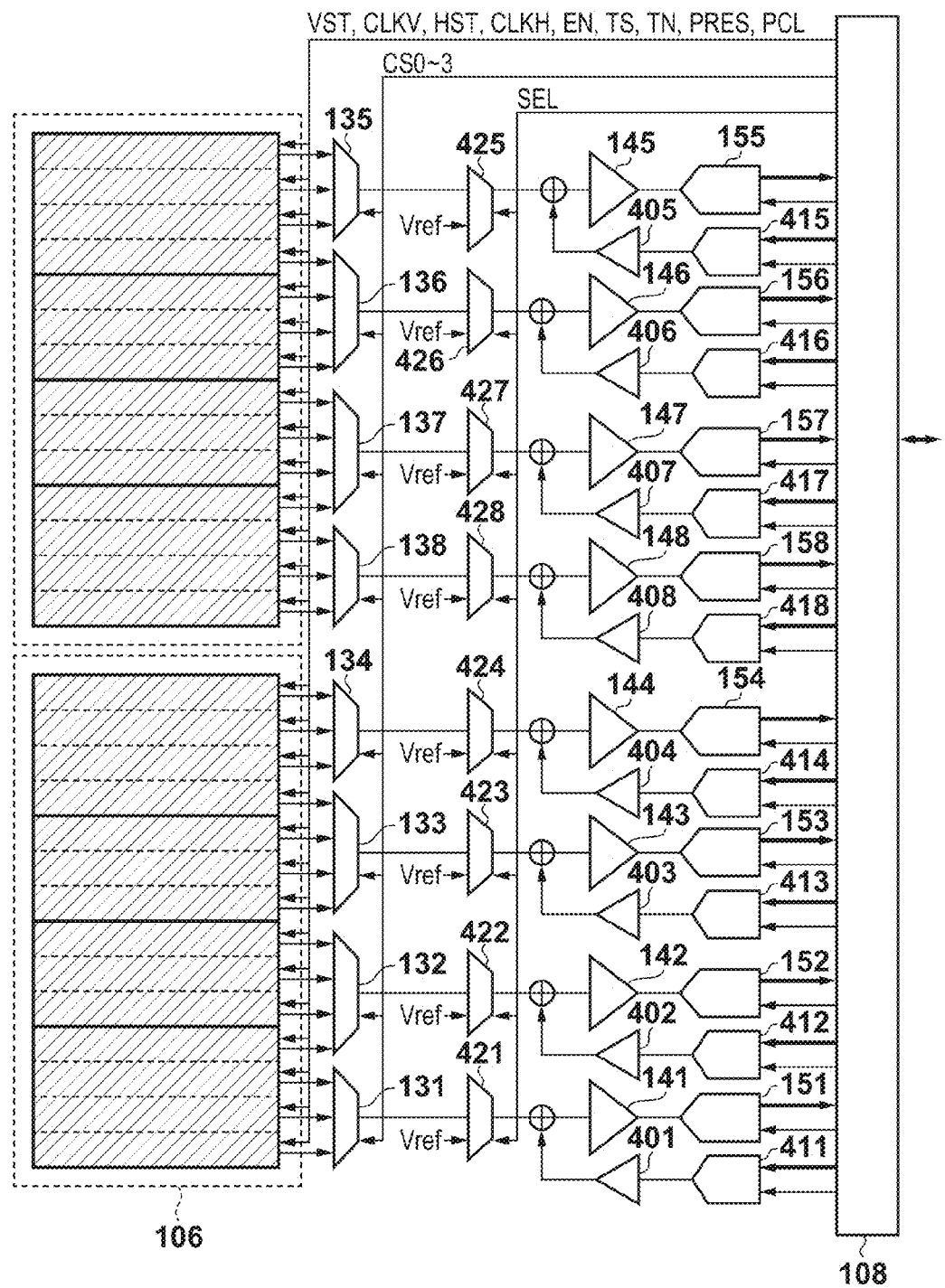

IMAGING APPARATUS, CONTROL METHOD THEREFOR, AND STORAGE MEDIUM

BACKGROUND OF THE INVENTION

1. Field of the Invention

The present invention relates to an imaging apparatus and a control method therefor and, more particularly, to a technique of reducing image artifacts upon imaging an object by irradiating it with radiation.

2. Description of the Related Art

In recent years, in the field of digital X-ray imaging apparatuses, a large-area flat panel type radiation imaging apparatus of a non-scaled optical system using photoelectric conversion elements has been widely used, instead of an image intensifier, for the purpose of increasing the resolution, decreasing the volume, and suppressing image distortion.

As a flat panel sensor of a non-scaled optical system which is used for a radiation imaging apparatus, there is available a large-area flat panel sensor formed by two-dimensionally joining photoelectric conversion elements formed on a silicon semiconductor wafer by a CMOS semiconductor manufacturing process. Japanese Patent Laid-Open No. 2002-026302 describes a method of manufacturing a large-area flat panel sensor by tiling a plurality of rectangular semiconductor substrates which are strip-shaped rectangular imaging elements obtained by cutting photoelectric conversion elements from a silicon semiconductor wafer. This method can obtain an imaging region for a large-area flat panel sensor, which is equal to or larger than the size of the silicon semiconductor wafer.

Japanese Patent Laid-Open No. 2002-344809 describes the circuit arrangement of each strip-shaped rectangular semiconductor substrate obtained by cutting photoelectric conversion elements. On each strip-shaped rectangular semiconductor substrate, two-dimensionally arrayed photoelectric conversion elements and vertical and horizontal shift registers as readout control circuits are arranged. External terminals (electrode pads) are provided near the horizontal shift register. Control signals and clock signals input from the external terminals control the vertical and horizontal shift registers on the rectangular semiconductor substrate to sequentially output values of the respective pixel arrays from the respective shift registers in synchronism with the clock signals.

Japanese Patent Laid-Open No. 2002-345797 describes an arrangement in which a sampling operation associated with photoelectric conversion is simultaneously performed for all pixels in a flat panel sensor formed by tiling a plurality of rectangular semiconductor substrates. This arrangement implements a collective electronic shutter and equalizes the accumulation times of the respective pixels, thereby preventing pixel value discontinuity that might be caused by the tiling of the rectangular semiconductor substrates.

It is well known, however, that semiconductors such as rectangular semiconductor substrates, A/D converters, and differential amplifiers which form a flat panel sensor as described above generally generate shot noise, thermal noise, and 1/f (flicker) noise. Especially in a semiconductor manufactured by a MOS process, 1/f noise is predominant in the low-frequency region. In the flat panel sensor formed by tiling the plurality of rectangular semiconductor substrates, 1/f noise is superimposed on digital image data for each block A/D converted by an A/D converter. Therefore, block-shaped artifacts occur in the captured image of the flat panel sensor.

In, for example, a dark image which has undergone FPN (fixed pattern noise) correction and has not been exposed to radiation, if no 1/f noise occurs, a very flat image shown in FIG. 11A is obtained. If, however, low-frequency 1/f noise occurs in each of the rectangular semiconductor substrates, differential amplifiers, and A/D converters, a block-shaped artifact for each A/D converter appears, as shown in FIG. 11B. Especially, the radiation imaging apparatus needs a wide dynamic range, and thus low noise is required for a readout circuit used for the radiation imaging apparatus.

SUMMARY OF THE INVENTION

The present invention has been made in consideration of the aforementioned problems, and provides a technique capable of reducing artifacts caused by 1/f noise.

The present invention in its first aspect provides an imaging apparatus including a radiation tube which irradiates an object with radiation, a plurality of photoelectric conversion elements which are arrayed in a matrix and each of which detects an intensity of radiation that has been transmitted through the object to output an electric signal corresponding to the intensity, a readout circuit which reads out the electric signals for each line of the matrix of photoelectric conversion elements in synchronism with a predetermined clock, amplifiers which amplify the read-out electric signals and output the amplified electric signals as a measurement value of the object, and a control unit which determines, based on a frame interval associated with imaging of the object, the number of output values to be measured, and inputs electric signals of a given value to the amplifiers to measure the determined number of output values during a time after the readout circuit performs a readout operation for the photoelectric conversion elements of one line and before the readout circuit performs a readout operation for the photoelectric conversion elements of the next line, calculates a difference between the measured output value and a predetermined reference value, and corrects a measurement value of one line of the object by increasing or decreasing the measurement value by the difference.

Further features of the present invention will become apparent from the following description of exemplary embodiments (with reference to the attached drawings).

BRIEF DESCRIPTION OF THE DRAWINGS

FIG. 8 is a block diagram schematically showing part of the arrangement of the radiation imaging apparatus;

DESCRIPTION OF THE EMBODIMENTS

Embodiments of the present invention will be described in detail below with reference to the accompanying drawings.

First Embodiment

Radiation Moving Image Capturing Apparatus

Figure 1:
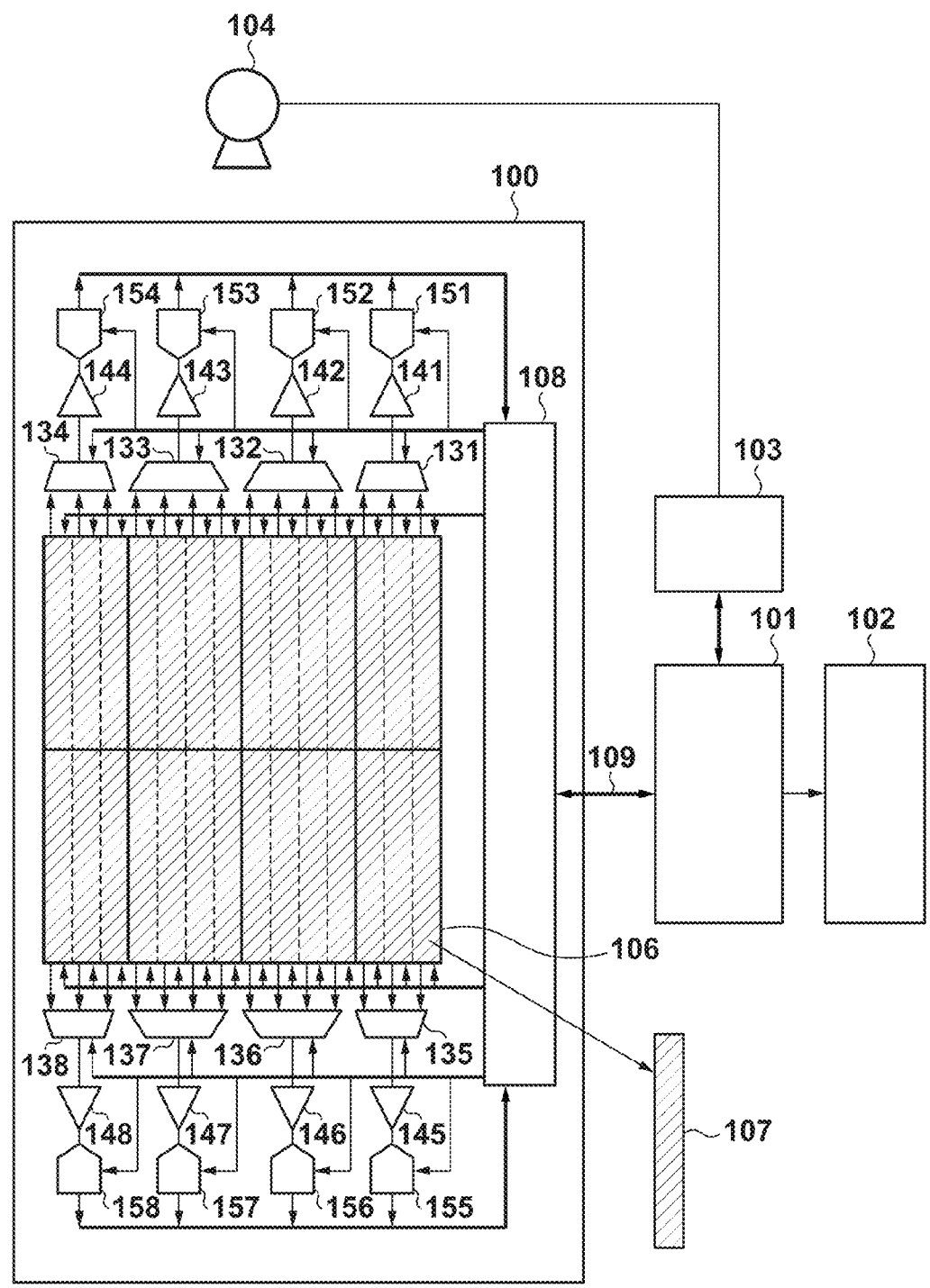
FIG. 1 is a block diagram schematically showing the overall system of a radiation moving image capturing apparatus.

FIG. 1 is a block diagram schematically showing the overall system of a large-area flat panel type radiation moving image capturing apparatus. Reference numeral 100 denotes a radiation imaging apparatus; 101, a system control apparatus (image processing apparatus); 102, an image display apparatus; 103, an X-ray generating apparatus; and 104, an X-ray tube (radiation tube). In an imaging operation, the system control apparatus 101 synchronously controls the radiation imaging apparatus 100 and X-ray generating apparatus 103. If the X-ray tube 104 irradiates an object (not shown) with X-rays (radiation) under the control of the X-ray generating apparatus 103, the X-rays pass through the object to reach the radiation imaging apparatus 100. In the radiation imaging apparatus 100, a scintillator (not shown) converts the radiation that has been transmitted through the object into visible light, which after photoelectric conversion according to the amount of light detected, is represented by a signal, which undergoes A/D conversion. The radiation imaging apparatus 100 transfers frame image data corresponding to the X-ray irradiation to the system control apparatus 101. After image processing, the image display apparatus 102 displays a radiation image in real time.

In the radiation imaging apparatus 100, reference numeral 106 denotes a flat panel sensor. In the example shown in FIG. 1, the flat panel sensor 106 is formed by tiling, on a flat base (not shown) in a matrix of 14 columns×2 rows, a plurality of strip-shaped rectangular semiconductor substrates 107 obtained by two-dimensionally cutting photoelectric conversion elements from a silicon semiconductor wafer. The photoelectric conversion element detects the intensity of radiation having been transmitted through an object, and outputs an electric signal corresponding to the intensity. A plurality of photoelectric conversion elements are arranged on the rectangular semiconductor substrate 107 in a matrix. The external terminals (electrode pads) (not shown) of the rectangular semiconductor substrates 107 arrayed in a matrix are arrayed in a line on each of the upper and lower side portions of the flat panel sensor 106. The electrode pads of the rectangular semiconductor substrates 107 are connected to external circuits through flying lead type printed circuit boards (not shown). Reference numerals 131 to 138 denote analog multiplexers which select pixel outputs from the connected rectangular semiconductor substrates according to control signals from an imaging unit control unit 108, and output the selected outputs to connected differential amplifiers 141 to 148, respectively. The differential amplifiers 141 to 148 respectively amplify and output the input electric signals (voltages in this embodiment). Reference numerals 151 to 158 denote A/D converters, each of which convert an analog signal from a corresponding one of the connected differential amplifiers 141 to 148 into a digital signal according to a synchronization clock output from the imaging unit control unit 108, and outputs the digital signal to the imaging unit control unit 108. The imaging unit control unit combines digital image data in each block, which have undergone A/D conversion by the A/D converters 151 to 158, into frame data, and transfers it to the system control apparatus 101. In this way, the electric signals output from the differential amplifiers 141 to 148 are output as measurement values of the captured image of the object.

Each of the strip-shaped rectangular semiconductor substrates 107 has a width of about 20 mm and a length of about 140 mm. The flat panel sensor 106 formed by tiling the substrates in a matrix of 14 columns×2 rows has a length of about 280 mm and a width of about 280 mm, that is, has a square shape with a side of about 11 inches. Note that the size of each rectangular semiconductor substrate 107, the number of rectangular semiconductor substrates 107, and the size of the flat panel sensor 106 are not limited to them.

(General Sampling Operation)

Figure 2:
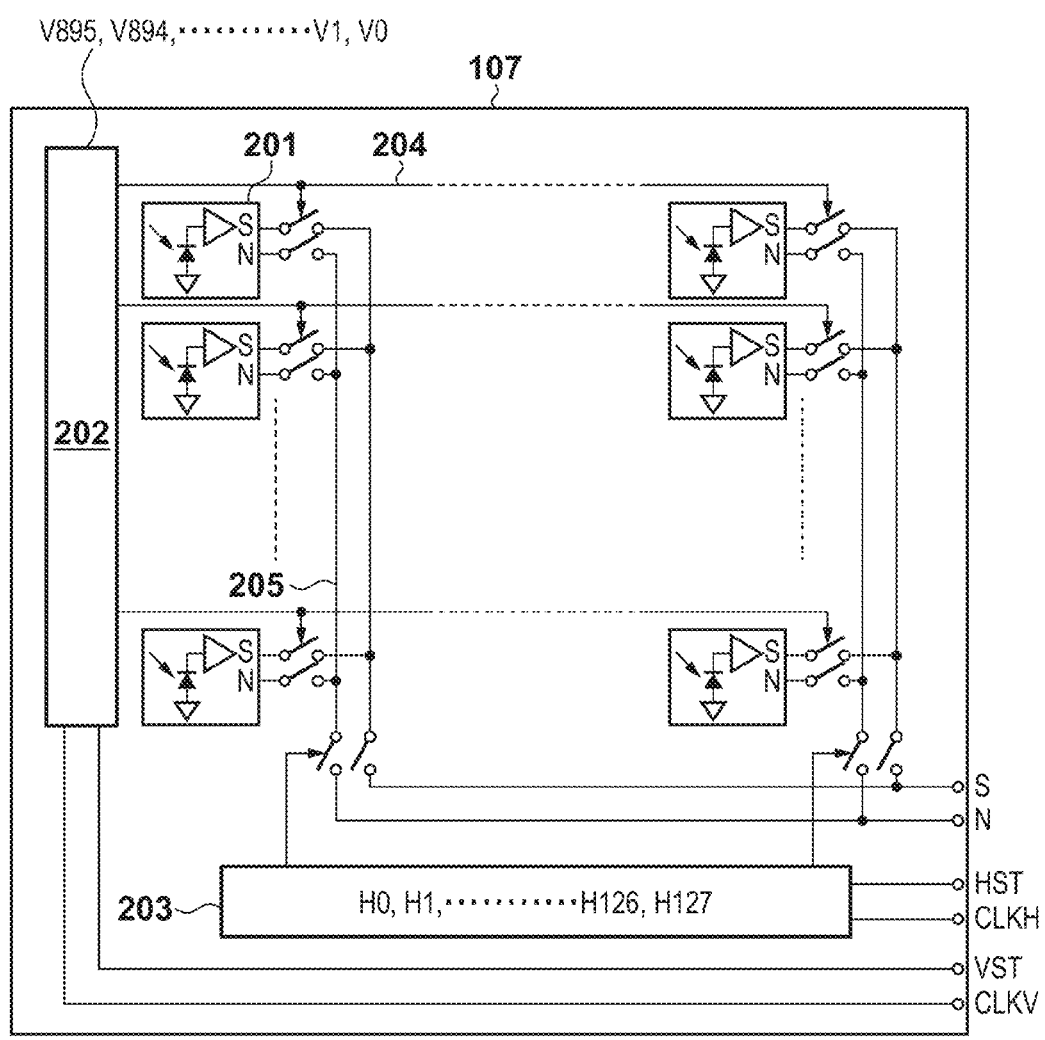
FIG. 2 is a block diagram schematically showing the internal arrangement of a rectangular semiconductor substrate.
Figure 3:
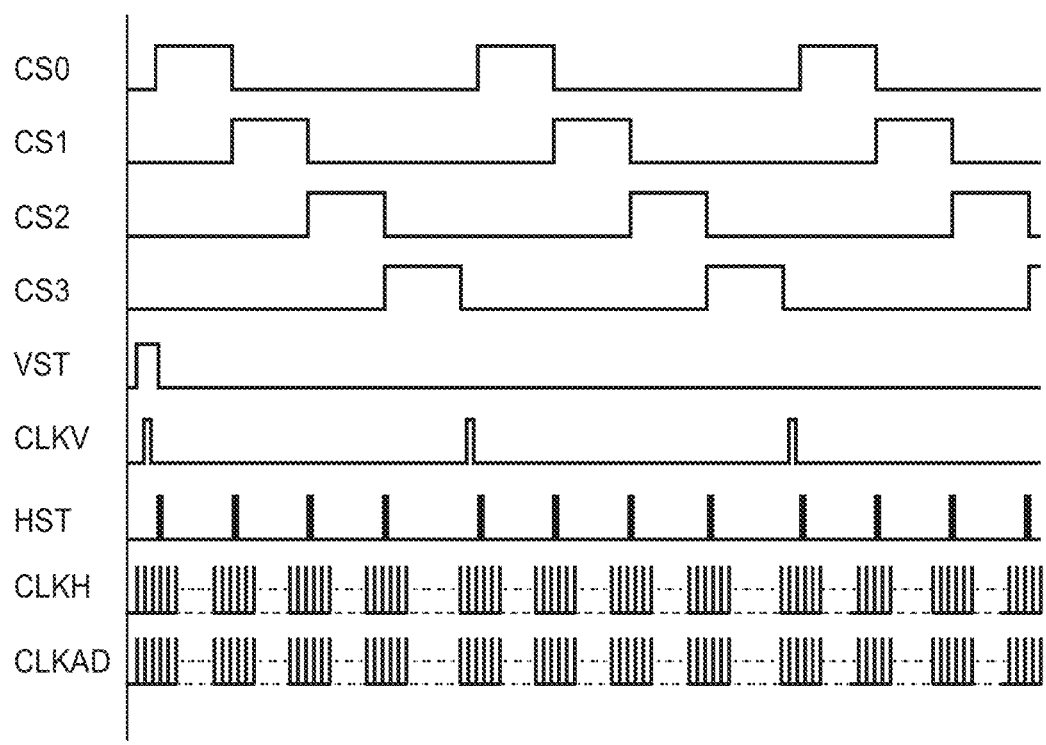
FIG. 3 is a timing chart showing an example of an image readout procedure.

A general procedure of reading out an image using the aforementioned arrangement will be described with reference to FIGS. 2 and 3. FIG. 2 is a block diagram schematically showing the internal arrangement of the rectangular semiconductor substrate 107. FIG. 3 is a timing chart showing an example of a procedure of reading out an image from the flat panel sensor 106 formed by tiling the rectangular semiconductor substrates 107.

Referring to FIG. 2, pixel circuits 201 including two-dimensionally arrayed photoelectric conversion elements, and a vertical shift register 202 and horizontal shift register 203 as readout control circuits are arranged on the rectangular semiconductor substrate 107. A horizontal shift register start signal HST, a vertical shift register start signal VST, a horizontal shift clock signal CLKH, and a vertical shift clock signal CLKV are input from the external terminals.

Referring to FIG. 3, when the signal CLKV rises while the signal VST is in the "H" state, the internal circuit of the vertical shift register 202 is reset. A signal in the "H" state is then output as an output V0 of the vertical shift register 202 to enable pixel outputs of one line controlled by a row control signal 204. When the signal CLKH rises while the signal HST is in the "H" state, the internal circuit of the horizontal shift register 203 is reset and a signal in the "H" state is then output as an output H0 of the horizontal shift register 203. The output of the pixel circuit 201 selected by the output H0 among the pixels of the one line enabled by the row control signal 204 is output to the analog output terminal. CLKH pulses are sequentially input to the horizontal shift register 203 to sequentially shift the output "H" to H0, H1, . . . , H126, and H127, thereby completing a readout operation of the pixels of one line corresponding to V0. The vertical shift clock signal CLKV is then input to the vertical shift register 202 to switch the output in the "H" state to V1. After that, a readout operation is performed for the pixels of one line corresponding to V1. These operations are sequentially repeated to perform a readout operation for all the pixels of the rectangular semiconductor substrate 107. In this way, readout processing of reading out the electric signals for each line of the matrix of the photoelectric conversion elements is executed in synchronism with a predetermined clock.

Since the pixel outputs of the rectangular semiconductor substrate 107 are sequentially output to the external analog output terminals in synchronism with the clock signal CLKH, the A/D converter performs A/D conversion according to an A/D conversion clock CLKAD synchronous with the clock signal CLKH.

Figure 4:
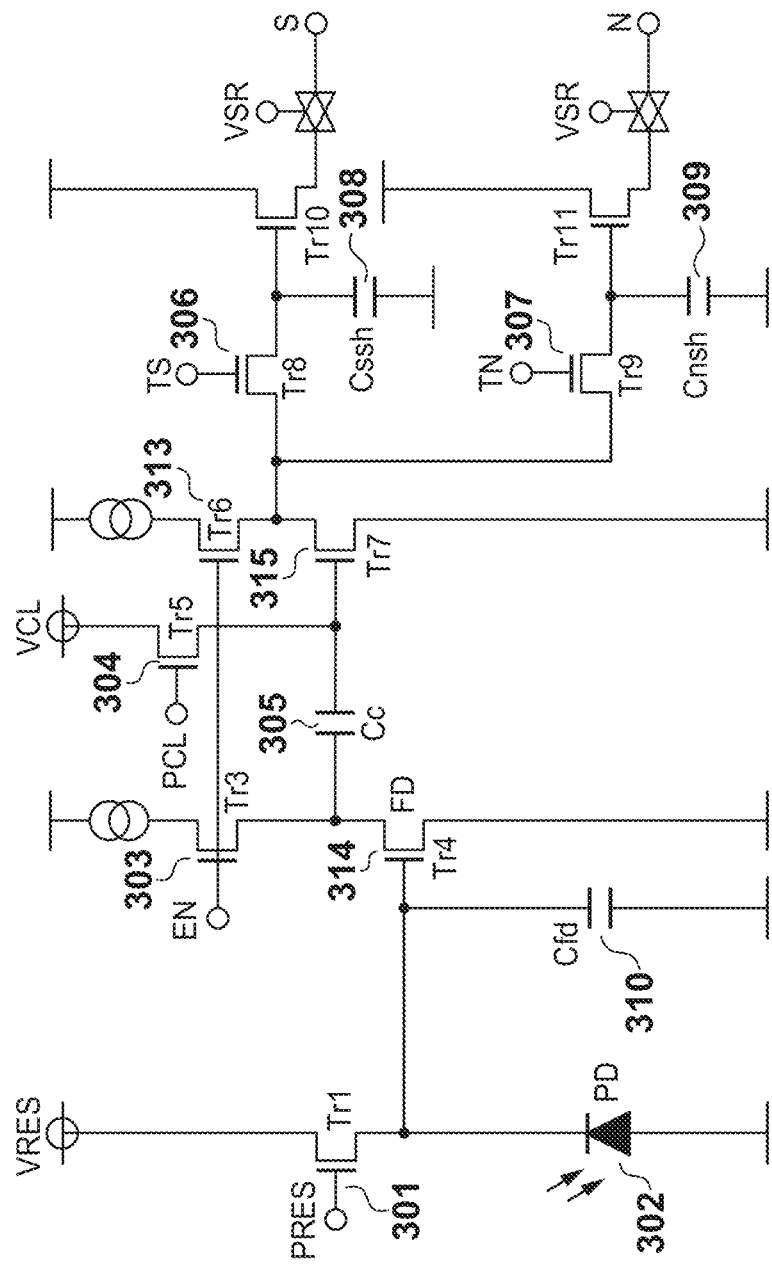
FIG. 4 is a circuit diagram schematically showing an equivalent circuit for one pixel of the rectangular semiconductor substrate.

FIG. 4 is a circuit diagram showing one pixel on the tiled rectangular semiconductor substrate 107. Referring to FIG. 4, reference numerals 301, 303, 304, 306, 307, and 313 denote switching MOS transistors (to be simply referred to as "switches" hereinafter). A reset voltage VRES is applied to the switch 301 to reset a photodiode unit 302 and a floating diffusion capacitor (capacitor) 310. The switch 303 activates a MOS transistor 314 functioning as a floating diffusion amplifier. The switch 313 activates a MOS transistor 315 functioning as a source follower amplifier. The switch 304 is combined with a clamp capacitor (capacitor) 305 to form a clamp circuit, which can remove kTC noise (reset noise) generated by the photodiode unit 302. The switch 306 samples and holds a signal voltage corresponding to the amount of light. The switch 307 samples and holds a clamp voltage VCL.

When the switch 306 is turned on, a capacitor 308 accumulates electric charges. When the switch 307 is turned on, a capacitor 309 accumulates electric charges. The capacitor 309 accumulates the electric charges of the clamp voltage VCL, that is, noise and dark current components. The capacitor 308 accumulates electric charges obtained by adding the noise and dark current components to the voltage of the photodiode unit 302. That is, subtracting the electric charges accumulated in the capacitor 308 from those accumulated in the capacitor 309 yields a voltage corresponding to the amount of light from the photodiode unit 302. Each of the differential amplifiers 141 to 148 shown in FIG. 1 performs this subtraction operation.

The pixel value data obtained from the rectangular semiconductor substrate 107 contains the noise components of the photodiode unit 302 which cannot be removed by subtracting the electric charges accumulated in the capacitor 309 from those accumulated in the capacitor 308. For this reason, such pixel value data is corrected by an FPN image using, as fixed pattern noise (FPN), pixel value data imaged without irradiation of radiation.

Figure 5:
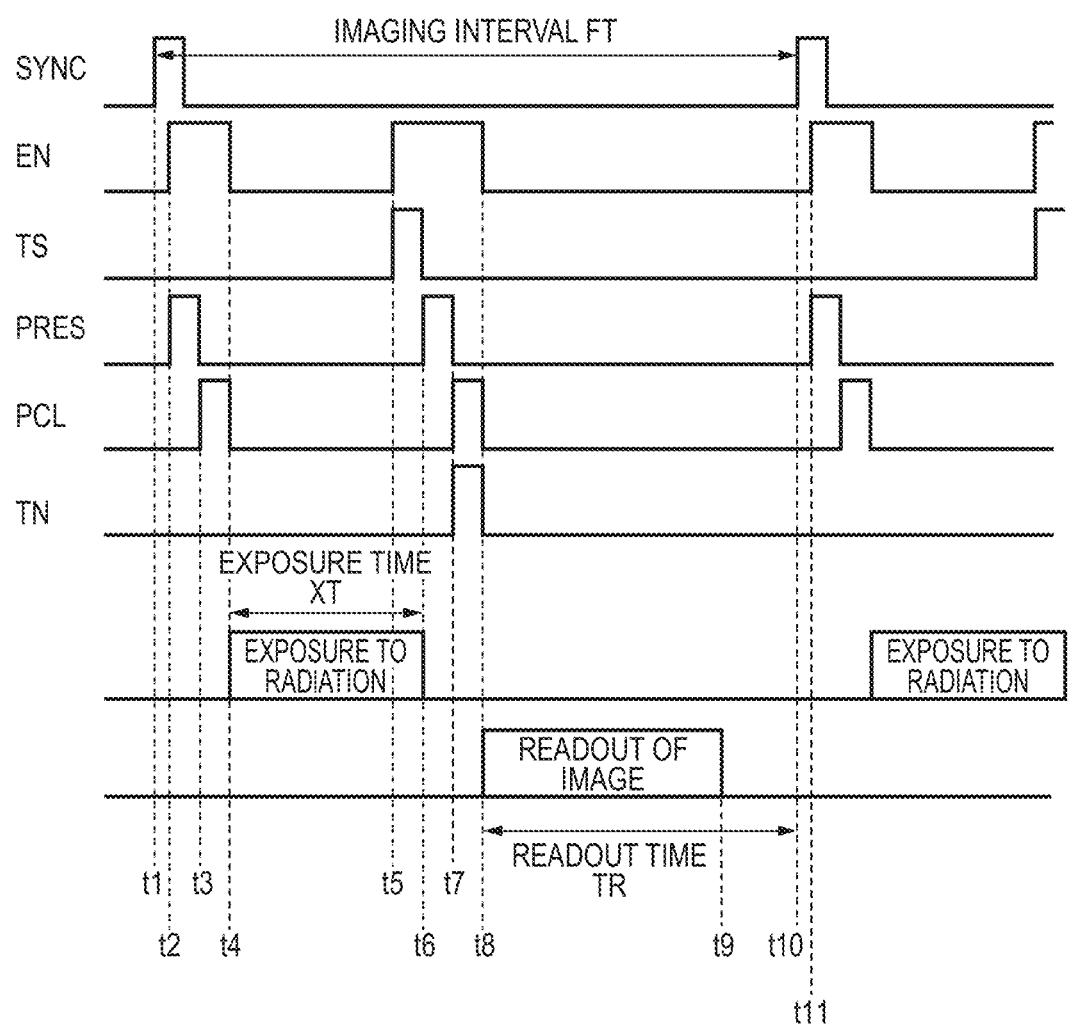
FIG. 5 is a timing chart showing rectangular semiconductor substrate control signals.

A sampling operation when a moving image is captured by intermittently irradiating an object with pulsed radiation will be described with reference to FIGS. 4 and 5. When a synchronization signal SYNC is input from the system control apparatus 101 at a time t1, in order to start accumulation of radiation, the system control apparatus 101 turns on the switches 303 and 313 to activate the pixel circuit on the sensor chip at a time t2. At the same time, a signal PRES is set at high level to turn on the switch 301, and the reset voltage VRES is applied to the floating diffusion capacitor 310, thereby resetting the sensor. The interval at which the synchronization signal SYNC is input corresponds to an imaging interval FT of a moving image.

After the reset state is cancelled by turning off the switch 301 at a time t3, a signal PCL is set at high level to turn on the switch 304, and then the clamp voltage VCL is applied to the capacitor 305. At a time t4, the switches 304 and 301 are turned off to terminate a pixel reset operation and start accumulation of the photodiode unit 302, thereby causing the radiation imaging apparatus 100 to detect exposure to radiation.

The object is irradiated with pulsed radiation for a predetermined period of time. Therefore, to minimize the influence of noise components of the photodiode unit 302, accumulation is terminated when a time corresponding to the irradiation time elapses. At a time t5, a signal EN is set at high level to turn on the switches 303 and 313, thereby activating the pixel circuit on the sensor chip. At the same time, the switch 306 is turned on to cause the capacitor 308 to sample and hold the voltage of the photodiode unit 302. At a time t6, the switch 306 is turned off to terminate sampling and holding, thereby disabling exposure to radiation. After that, the switch 301 is turned on to apply the reset voltage VRES to the floating diffusion capacitor 310, thereby resetting the sensor. At a time t7, the switch 301 is turned off and the switch 304 is then turned on, thereby applying the clamp voltage VCL to the capacitor 305. Then, the switch 307 is turned on to cause the capacitor 309 to sample and hold the clamp voltage VCL.

At a time t8, all of the switches 307, 304, 303, and 313 are turned off, thereby terminating sampling and holding. The voltages sampled and held by the capacitors 308 and 309 are sequentially output to the outside by scanning the vertical and horizontal shift registers.

Although it is possible to change these driving timings according to settings, the set driving operation is repeated during an imaging operation to simplify control. That is, upon detecting the synchronization signal SYNC again at a time t9, the switch 303 is turned on to activate the pixel circuit on the sensor chip at a time t10, thereby repeating the above operation.

Similarly to the arrangement described in Japanese Patent Laid-Open No. 2002-345797, simultaneously performing the above sampling operation for all pixels implements a collective electronic shutter and equalizes the accumulation times of the respective pixels, thereby preventing pixel value discontinuity caused by tiling of the rectangular semiconductor substrates. The sampled and held voltages are read out as analog signals by scanning the horizontal and vertical shift registers for each rectangular semiconductor substrate. The A/D converter converts the analog signal into a digital signal to generate a digital image signal. Performing scanning during exposure to radiation can cope with a high frame rate when capturing a moving image because it is possible to perform accumulation of radiation and scanning at the same timing.

(Sampling Operation)

As described above, however, the aforementioned general image sampling operation cannot process block-shaped artifacts caused by 1/f noise (flicker noise) generated by the semiconductors forming the radiation imaging apparatus 100. To solve this problem, in this embodiment, before imaging an object, the outputs of the differential amplifiers 141 to 148 when reference voltage signals are input to the amplifiers are obtained in advance. A captured image is then corrected with the differences between the obtained outputs and outputs when the reference voltage signal is input to the amplifiers. Note that since the 1/f noise changes with time, it is necessary to correct measurement values based on samples measured at a timing near the image obtaining timing. In this embodiment, offset sampling is performed for each line during a time which is included in the imaging interval but is actually unnecessary for an imaging operation. According to this embodiment, this operation can effectively and efficiently reduce the 1/f noise.

More specifically, to perform offset sampling in a circuit from a circuit outside the sensor, that is, a multiplexer up to the control unit through the differential amplifier and A/D converter, switching processing in the multiplexer is required. In this embodiment, since it is possible to perform this switching processing during a blanking period, there is almost no influence or a very small influence on a delay in a readout operation due to the switching processing. If, for example, offset sampling is performed for each pixel, a correction value can be obtained at high accuracy while the switching processing has an influence on a readout time. The aforementioned offset sampling processing for each line according to the embodiment can efficiently suppress the influence of noise while suppressing a delay in readout time.

A sampling operation when a moving image is captured by intermittently irradiating an object with pulsed radiation will be described below with reference to FIGS. 4 and 6 to 8.

Figure 6:
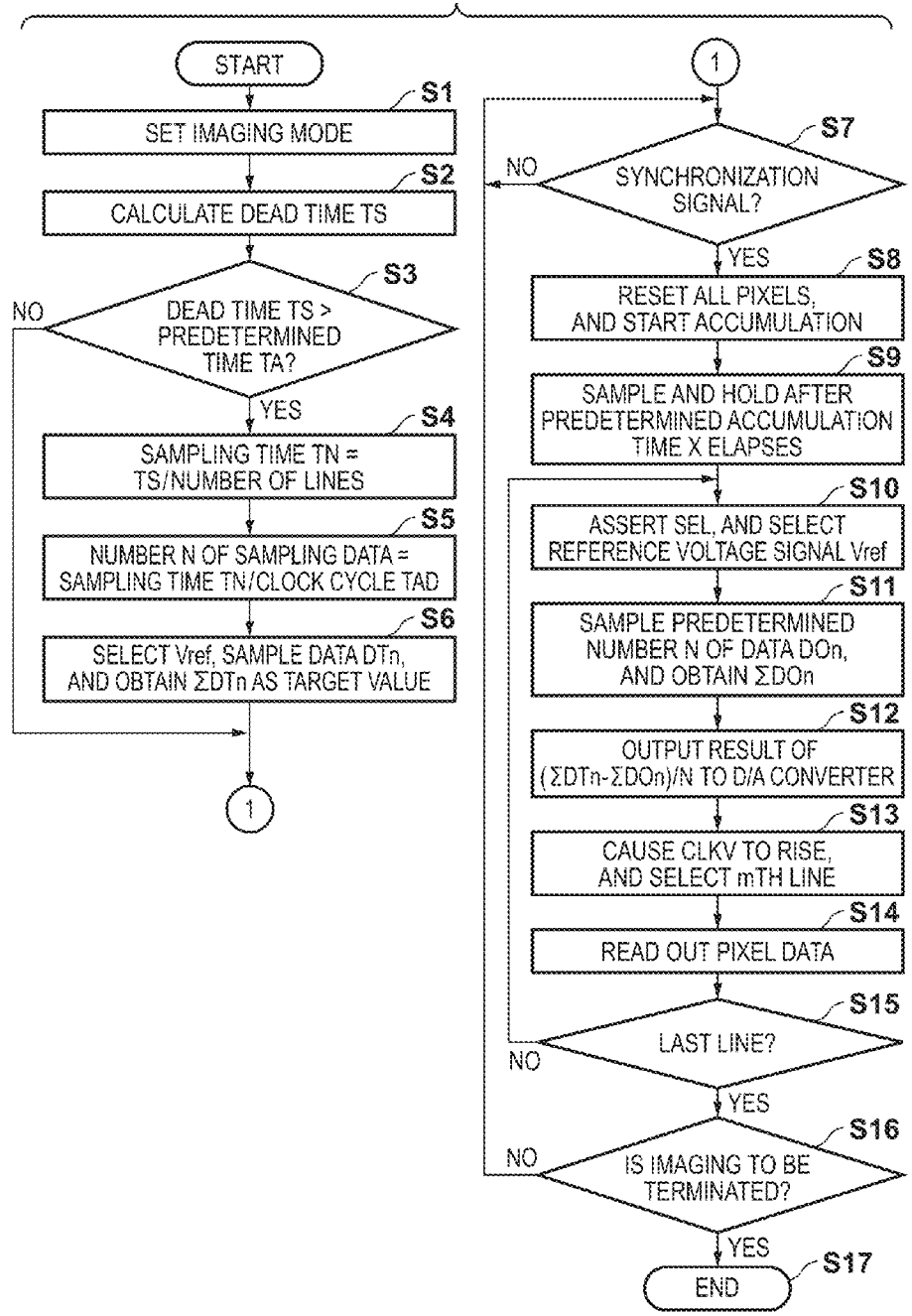
FIG. 6 is a flowchart illustrating a procedure of controlling the rectangular semiconductor substrate.

In steps S1 to S6 of FIG. 6, processing of generating a target value for offset correction by performing exposure to radiation while no object exists is executed. If an imaging operation is performed in one imaging mode, the processing in steps S1 to S6 need only be executed once before imaging an object and need not be executed every time an object is imaged.

In step S1 of FIG. 6, the radiation imaging apparatus 100 starts an operation in an imaging mode set by the system control apparatus 101. This imaging mode includes a frame rate indicating an imaging interval, an accumulation time for accumulating radiation, and size information of an output image.

Figure 7A:
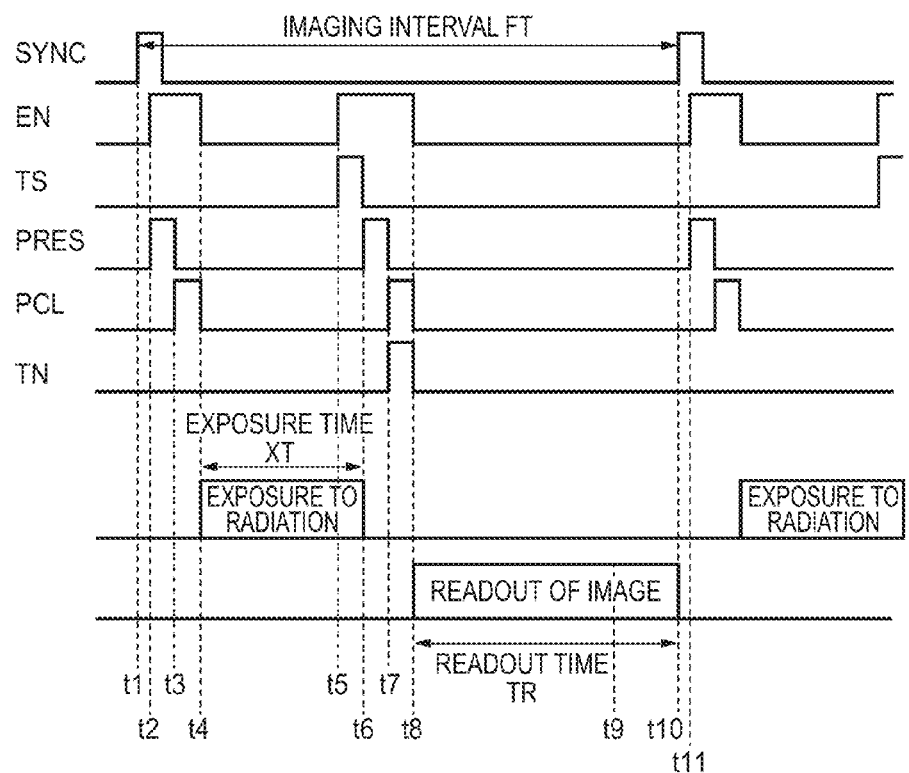
FIGS. 7A and 7B are timing charts showing a sampling operation when a moving image is captured by intermittently irradiating an object with pulsed radiation.

In step S2, a dead time (dead time TS) during an imaging cycle is calculated based on the set imaging mode. The dead time TS indicates a time during which processing necessary for an imaging operation is not performed but which is included in the imaging interval. Referring to FIG. 5, the dead time TS corresponds to the time from the time t9 to the time t10. In FIG. 7A, for example, the dead time TS can be calculated by subtracting, from the imaging interval FT, the time from the time t2 to the time t4 for a reset operation, an exposure time XT for accumulating radiation, the time from the time t6 to the time t8 for sampling pixel data in the sensor chip, and (the number of pixel data to be sampled by the differential amplifiers 141 to 148)×(a clock cycle TAD input to the A/D converters).

In step S3, it is determined whether the dead time TS is longer than a predetermined time TA, thereby checking whether offset correction data can be sampled. If the time TS is not longer than the time TA, that is, it is impossible to have the predetermined time TA within the imaging interval (NO in step S3), a short imaging interval (high frame rate) is determined, and the process advances to step S7. In this case, offset data is not sampled, and offsets occurring in the image are not corrected. However, the imaging interval is short, the image is displayed at high speed, and thus image artifacts are not so noticeable. This is because the 1/f noise has a characteristic that its power is inversely proportional to the frequency.

If the time TS is longer than the time TA (YES in step S3), the process advances to step S4. In step S4, the calculated time TS is divided by the number (896 in the example of FIG. 2) of lines in the vertical direction determined based on the image size, thereby calculating the time TN for sampling the offset data for one line. In step S5, the calculated sampling time TN for one line is divided by the clock cycle input to the A/D converters. Based on the division result, the number N of offset data to be sampled for one line is determined. In the following description, the number N of data to be sampled for one line is set to the value obtained by dividing the time TN by the clock cycle. However, a value smaller than the result of the division operation may be set as the number N of sampling data.

In step S6, a data generation operation for setting a target value in offset correction is performed before an imaging operation. Note that in this embodiment, a target value for offset correction is generated while no exposure to radiation is performed. As will be described in the second embodiment, it is also possible to generate a target value while exposure to radiation is performed. The data generation operation will be described with reference to FIG. 8. FIG. 8 is a schematic block diagram showing an example of the arrangement of the radiation imaging apparatus to which an offset correction circuit has been added. Referring to FIG. 8, an offset correction circuit formed by multiplexers 421 to 428, D/A converters 411 to 418, and amplifiers 401 to 408 is added to the arrangement of the radiation imaging apparatus 100 shown in FIG. 1.

As described above with reference to FIG. 2, the radiation imaging apparatus 100 includes a plurality of blocks each including:

the multiplexers 131 to 138, each of which outputs one of the output signals of the rectangular semiconductor substrates 107 based on an instruction from the imaging unit control unit 108;

the differential amplifiers 141 to 148; and the A/D converter 151 to 158.

In each block, each of the multiplexers 421 to 428 selects one of the output signal of a corresponding one of the multiplexers 131 to 138 and a reference voltage signal Vref as a predetermined voltage. Each of the D/A converters 411 to 418 converts offset correction data calculated by the imaging unit control unit 108 into an analog signal, and a corresponding one of the amplifiers 401 to 408 amplifies the analog signal.

Note that although FIG. 8 shows a circuit in which blocks each formed by the multiplexer, D/A converter, amplifier, and the like are arrayed in the vertical direction in order to readily identify the flat panel sensor 106, the blocks are actually arrayed, as shown in FIG. 1.

To generate a target value for offset correction, the imaging unit control unit 108 controls each of the multiplexers 421 to 428 to output the reference voltage signal Vref. When each of the multiplexers 421 to 428 starts to output the reference voltage signal Vref, the imaging unit control unit 108 samples the number N of data output from each of the A/D converters 151 to 158, which has been calculated in step S5. For each of the A/D converters 151 to 158, the sum ΣDTn of the N target value data DTn is calculated.

The values of the sampled data vary due to noise occurring in the multiplexers 421 to 428, the differential amplifiers 141 to 148, and the A/D converters 151 to 158. It is known that the accuracy of an average value statistically improves as the number of sampling data increases. Therefore, the number of data to be sampled may be determined to be an integer (M) multiple of N, and a target value may be obtained by dividing the total value by M.

In steps S7 to S9, according to a procedure similar to the general sampling operation, exposure to radiation, photoelectric conversion, and accumulation and holding of electric charges are performed. In step S7, a synchronization signal for the first image input from the system control apparatus 101 is detected. When the first synchronization signal SYNC is input from the system control apparatus 101 at the time t1 in FIG. 7A, the switches 303 and 313 shown in FIG. 4 are turned on at the time t1 to activate the pixel circuit on the sensor chip, thereby starting accumulation of radiation. At the same time, the signal PRES is set at high level to turn on the switch 301. Furthermore, the reset voltage VRES is applied to the photodiode unit 302 and floating diffusion capacitor 310 to reset the sensor (step S8).

After the reset state is cancelled by turning off the switch 301 at the time t3, the signal PCL is set at high level to turn on the switch 304, and then the clamp voltage VCL is applied to the clamp capacitor (capacitor) 305. At the time t4, the switches 304 and 301 are turned off to terminate a pixel reset operation. This processing starts accumulation of the photodiode unit 302, and causes the radiation imaging apparatus 100 to detect exposure to radiation.

The object is irradiated with pulsed radiation for a predetermined period of time. Therefore, to terminate accumulation when a time corresponding to the irradiation time elapses, the signal EN is set at high level at the time t5. The switches 303 and 313 are then turned on and the pixel circuit on the sensor chip is activated. At the same time, the switch 306 is turned on to cause the capacitor 308 to sample and hold the voltage of the photodiode unit 302. At the time t6, the switch 306 is turned off to terminate sampling and holding, thereby disabling exposure to radiation. After that, the switch 301 is turned on to apply the reset voltage VRES to the floating diffusion capacitor 310, thereby resetting the sensor. After the switch 301 is turned off at the time t7, the switch 304 is turned on to apply the clamp voltage VCL to the capacitor 305. Next, the switch 307 is turned on to cause the capacitor 309 to sample and hold the clamp voltage VCL. At the time t8, the switches 307, 304, 303, and 313 are turned off, thereby terminating sampling and holding (step S9).

Figure 7B:
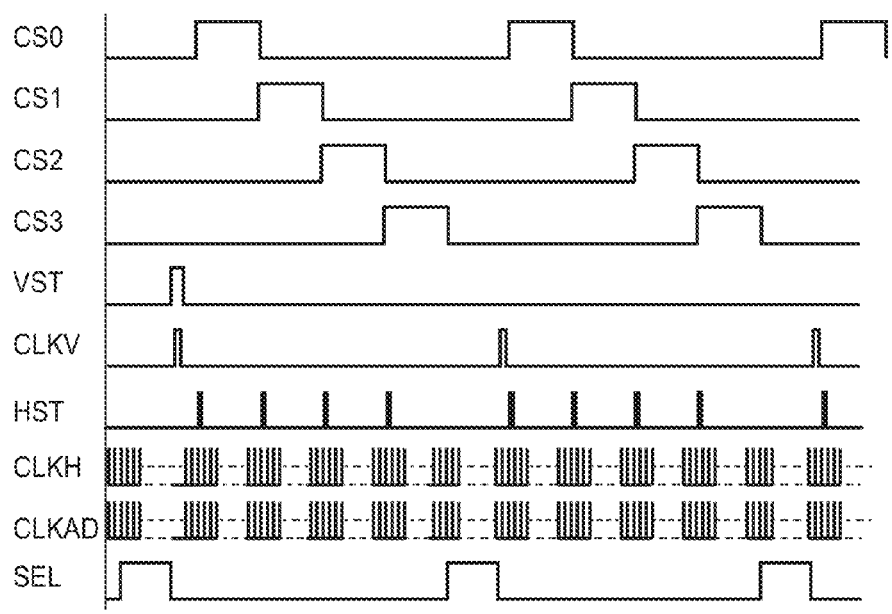

In steps S10 to S15, data for offset correction are obtained while sequentially outputting, to the outside, the voltages sampled and held by the capacitors 308 and 309 by scanning the vertical and horizontal shift registers. This operation will be described with reference to FIGS. 6 and 7. FIG. 7B shows, in detail, the operation from the time t8 to the time t9 shown in FIG. 7A.

In step S10 of FIG. 6, the imaging unit control unit 108 sets a signal SEL in the "H" state, and selects the reference voltage signal Vref as the input of each of the multiplexers 421 to 428. Selecting the reference voltage signal Vref makes it possible to measure, as an offset from the target value, the 1/f noise occurring in the multiplexers 421 to 428, differential amplifiers 141 to 148, and A/D converters 151 to 158.

The process advances to step S11, in which the predetermined number N of output data DOn of each of the A/D converters 151 to 158 are sampled and the sum=ΣDOn is obtained. In step S12 of FIG. 6, the imaging unit control unit 108 subtracts ΣDOn from the sum ΣDTn of the target values obtained in step S6, and divides the obtained value by the number N of sampling data, thereby obtaining a correction value. The obtained correction value indicates an offset from the target value, and the imaging unit control unit 108 outputs the obtained correction value to a corresponding one of the D/A converters 411 to 418. The output correction value is digital data, and each of the D/A converters 411 to 418 converts the digital data into an analog signal, which then undergoes predetermined analog signal processing via a corresponding one of the amplifiers 401 to 408. The output signal of each of the amplifiers 401 to 408 is added to the output signal of a corresponding one of the multiplexers 421 to 428 by a corresponding one of addition circuits 431 to 438, thereby correcting an offset. If, for example, 1/f noise occurs and an offset becomes larger, the measurement value ΣDOn becomes larger with respect to the target value ΣDTn and thus the result in step S12 becomes negative, reducing the offset to be superimposed on the output signal of each of the multiplexers 421 to 428.

The imaging unit control unit 108 sets the signal SEL in the "L" state to select the multiplexers 131 to 138. Because the current line is the first line, the signal VST is set in the "H" state in FIG. 7B, thereby causing the signal CLKV to rise in step S13. When the signal CLKV rises, the internal circuit of the vertical shift register 202 shown in FIG. 2 is reset. "H" is output as the output V0 of the vertical shift register 202 to select one line to be controlled by the row control signal 204, thereby enabling pixel outputs corresponding to the one line. When the signal CLKH rises while the signal HST is in the "H" state, the internal circuit of the horizontal shift register 203 is reset and "H" is output as the output H0 of the horizontal shift register 203. The output of the pixel circuit 201 selected by the output H0 among the pixels of the one line enabled by the row control signal 204 is output to the analog output terminal. CLKH pulses are sequentially input to the horizontal shift register 203 to sequentially shift the output "H" to H0, H1, . . . , H126, and H127, thereby completing a readout operation for the one line. In step S14, the imaging unit control unit 108 sequentially sets signals CS0 to CS3 in the "H" state as shown in FIG. 7B to switch between the outputs of the rectangular semiconductor substrates 107 connected to the multiplexers 131 to 138, thereby performing an operation of reading out pixel data.

In step S15 of FIG. 6, the imaging unit control unit 108 determines whether the current line is the last line. If the current line is the last line, the process advances to step S16. In this example, since the current line is the first line, the process advances to step S10 to start an offset correction operation for the next line. These operations are sequentially repeated to read out the pixels of the rectangular semiconductor substrate 107. In step S16, it is determined whether the imaging operation is to be terminated. If it is determined that the imaging operation is not to be terminated, the process advances to step S10 and an imaging operation for a next image is performed; otherwise, the process advances to step S17 and the imaging operation is terminated. The readout operation is conventionally completed at the time t9, as shown in FIG. 7A. However, the aforementioned operations complete the operation of reading out all the pixel data at the time t10 by using the dead time from the time t9 to the time t10 as a time for sampling the data for offset correction for each line.

As described above, in this embodiment, an electric signal of a given value is input to each of the differential amplifiers 141 to 148 to measure an output value during a time after a readout operation is performed for the photoelectric conversion elements of one line and before a readout operation is performed for the photoelectric conversion elements of the next line. The difference between the measured output value and the target value (reference value) obtained in step S6 is calculated, and each measurement value of one line of the object is corrected by increasing or decreasing it by the calculated difference. According to this embodiment, therefore, it is possible to effectively reduce the influence of the 1/f noise for each line.

Furthermore, in this embodiment, a plurality of sampling operations are performed for each line, and correction is performed using the average value of the sampling results, thereby achieving image correction at high accuracy. In this embodiment, the number of output values to be measured is determined based on the time (dead time) unnecessary for imaging an object, which is included in the frame interval associated with imaging of the object, and the number of lines of the matrix of the photoelectric conversion elements. As described above, in this embodiment, offset sampling is performed for each line during the time which is included in the imaging interval but is actually unnecessary for an imaging operation, thereby efficiently reducing the 1/f noise at high accuracy.

In the arrangement shown in FIG. 1, for example, the number of pixels of the rectangular semiconductor substrate 107 is 128×896=114688 and the horizontal shift clock signal CLKH has a frequency of 20 MHz. In the arrangement shown in FIG. 1, three or four rectangular semiconductor substrates 107 are connected to each of the analog multiplexers 131 to 138, and thus a readout time TR is a time required to scan four rectangular semiconductor substrates 107. Therefore, the time TR is given by:

$$TR=114688 \times 1/20M \times 4 = \text{about } 23 \text{ ms}$$

If the frame rate is 15 FPS, the imaging interval FT is given by:

$$FT=1/15=66.7 \text{ ms}$$

If the accumulation time XT of a radiation signal is 16 ms, the time from the time t1 to the time t4 is 1 ms, and the time from the time t6 to the time t8 is 1 ms, then $$XT+TR=16 \text{ ms}+1 \text{ ms}+1 \text{ ms}+23 \text{ ms}=41 \text{ ms}<FT\ 66.7 \text{ ms}$$

The dead time from the time t9 to the time t10 is thus 66.7 ms−41 ms=25.7 ms.

The time for sampling data for offset correction for one line is obtained by dividing the dead time by the number of lines which is 896, given by:

$$25.7 \text{ ms} \div 896 \text{ lines} = 0.029 \text{ ms}$$

Assume that the clock of the A/D converter has a frequency of 20 MHz. In this case, the cycle is 50 ns. Therefore, the number of data which can be sampled within the above data sampling time is about 580. If the frame rate is 10 FPS, the number of data which can be sampled for each line is about 1300.

As described above, as the frame rate decreases, the number of data can be increased, thereby statistically improving the accuracy of the average value. Increasing the accuracy of correction data can further reduce artifacts, thereby outputting a high-quality radiation image.

To obtain an offset correction value, $\Sigma DTn-\Sigma D$ is divided by N to output an average value as a correction value. However, each of the amplifiers 401 to 408 may have a gain of 1/N to calculate an average. With this arrangement, a resolution below that of the A/D converters 151 to 158 is obtained, thereby allowing correction at higher accuracy.

In addition, in this embodiment, each of the multiplexers 131 to 138 sequentially selects the three or four rectangular semiconductor substrates 107. However, one differential amplifier, one A/D converter, and one offset correction circuit may be provided for one rectangular semiconductor substrate 107. With this arrangement, it is possible to reduce 1/f noise even in a moving image with a high frame rate.

Second Embodiment

In the first embodiment, the sampling operation when a moving image is captured by intermittently irradiating an object with pulsed radiation has been described. A similar method is applicable to a case in which a moving image is captured by continuously irradiating an object with radiation.

Figure 9:
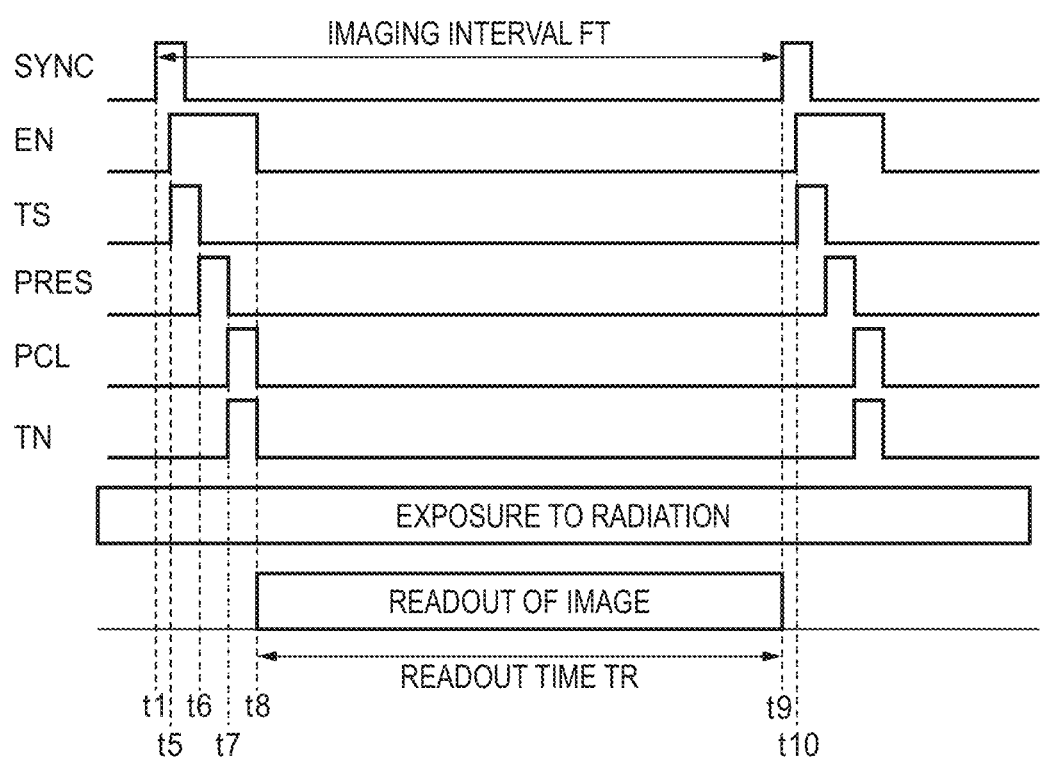
FIG. 9 is a timing chart showing a sampling operation when a moving image is captured by continuously irradiating an object with radiation.

FIG. 9 is a timing chart when a moving image is captured by continuously irradiating an object with radiation. Referring to FIG. 9, the operation from the time t2 to the time t5 in FIG. 7A when a moving image is captured by intermittently irradiating an object with pulsed radiation, that is, the operation from when the sensor is reset until sampling starts is not performed, and the operation from the time t5 to the time t10 is repeated to continuously capture an image. For a given imaging interval, therefore, it is possible to largely increase the number N of sampling data for measuring an offset, as compared with the case in which a moving image is captured by intermittently irradiating an object with pulsed radiation. It is also possible to reduce artifacts.

Third Embodiment

In the aforementioned first embodiment, each of the multiplexers 421 to 428 selects the reference voltage signal in measuring the target value and offset. To the contrary, each of multiplexers 421 to 428 may select a corresponding one of multiplexers 131 to 138 in measuring a target value and offset, and calculate a correction value based on the output values of rectangular semiconductor substrates 107. The rectangular semiconductor substrate 107 according to this embodiment has a so-called optical black portion. The optical black portion is formed by a pixel without sensitivity to input radiation or a group of such pixels. The optical black portion is formed by depositing, onto the incident surface of the rectangular semiconductor substrate 107, a material such as aluminum which blocks visible light. A fluorescent material is then deposited onto the aluminum. This prevents visible light from being transmitted through aluminum even if the radiation is converted into visible light by the fluorescent material, and thus the light does not reach pixels under the aluminum. Note that the fluorescent material need not be deposited. Forming the optical black portion in a peripheral portion of a sensor, for example, in a region including the first pixel of each line increases the manufacturing efficiency.

Figure 10:
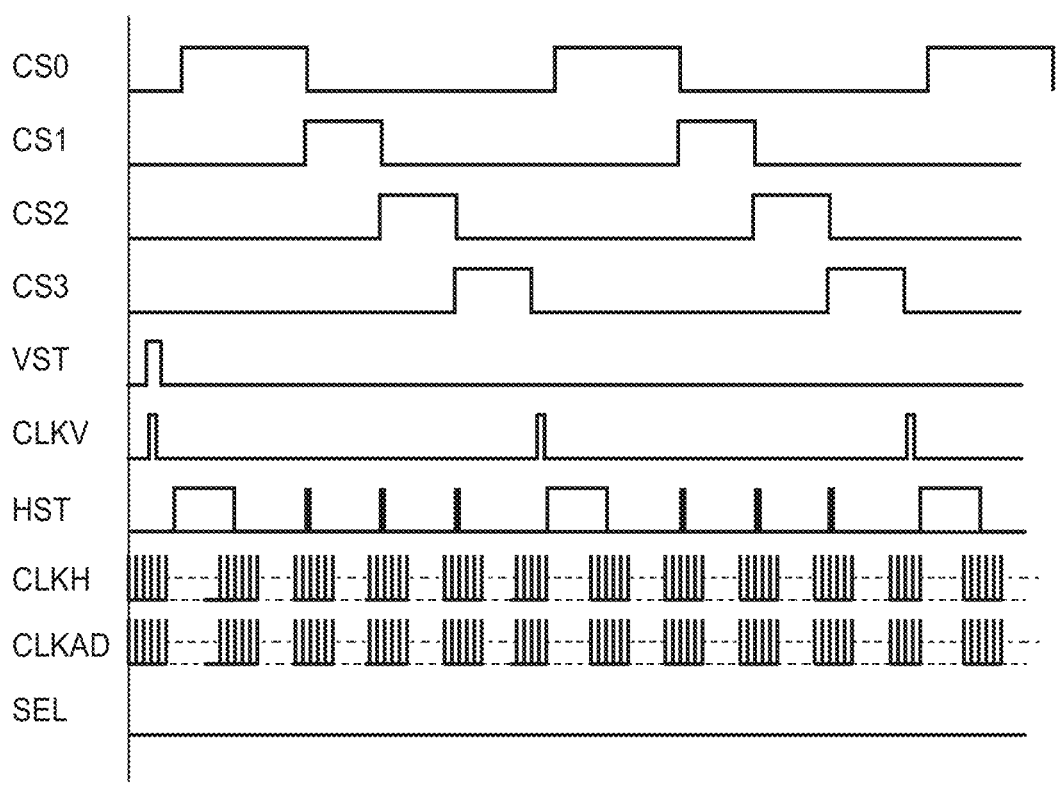
FIG. 10 is a timing chart showing rectangular semiconductor substrate control signals.
Figure 11A:
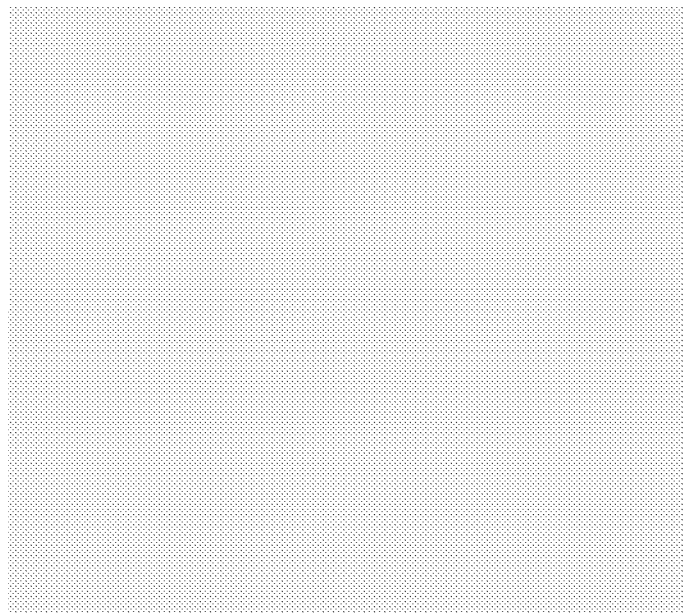
FIGS. 11A and 11B are views each showing an example of an image when 1/f noise occurs.
Figure 11B:
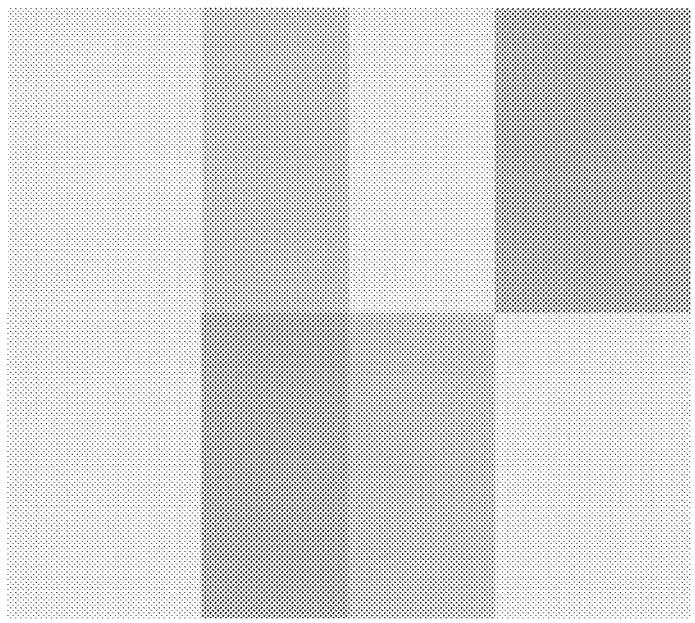

More specifically, as shown in FIG. 10, after a signal CLKV rises, signals CS0 and HST are set at high level for a time longer by a sampling time, and a predetermined number of pixel data of the pixels included in the optical black portion, for example, the first pixels of the respective lines of the sensor are sampled, thereby correcting an offset. Since the pixels output values independent of input radiation, the values serve as the reference potential according to the aforementioned embodiment. In this case, data of each line which have been sampled as target values are stored in a memory (not shown) for each line. The data are read out from the memory (not shown) for each line to calculate a correction value. This makes it possible to perform measurement including an offset due to 1/f noise occurring in the rectangular semiconductor substrate 107, and to reduce artifacts.

As described above, in each embodiment of the present invention, the number of sampling data for correcting an offset is determined based on an imaging interval which is determined based on an imaging mode. It is, therefore, possible to generate an image with reduced artifacts due to 1/f noise occurring in various semiconductors by effectively using the time during an imaging operation.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-170378, filed on Jul. 31, 2012 which is hereby incorporated by reference herein in its entirety.

What is claimed is:

1. An imaging apparatus for imaging an object based on X-rays that are irradiated from an X-ray tube and pass through the object, comprising:
   a plurality of pixel circuits which are arranged in a matrix and each of which outputs an analog signal corresponding to a received X-ray;
   a readout control circuit which controls a readout processing for reading out the analog signal for each line from the plurality of pixel circuits;
   a value-output circuit which outputs a measurement value corresponding to the analog signal or an analog reference value corresponding to a reference signal; and
   a correction circuit which applies an analog correction value signal for modifying the analog signal, derived from a predetermined reference value and a reference value which is outputted from the value-output circuit, corresponding to the analog reference signal during the period from a time at which the readout control circuit processes the readout processing for the plurality of pixel circuits for a certain line, to a time at which the readout control circuit processes the readout processing for the plurality of pixel circuits for a different line, to the value-output circuit as a signal to serve as the correction-value signal.

2. The apparatus according to claim 1, wherein each of the plurality of pixel circuits comprises a photodiode unit, a switch and a capacitor which sample and hold the analog signal corresponding to a voltage of the photodiode unit corresponding to the received X-ray.

3. The apparatus according to claim 2, wherein the value-output circuit outputs the reference value and the predetermined reference value during the time from the readout control circuit processes the readout processing for the plurality of pixel circuits for a certain line to the readout control circuit processes the readout processing for the plurality of pixel circuits for a different line, and wherein the correction circuit calculates the analog correction value signal based on a difference between an average value of the plurality of the reference values and the predetermined reference value.

4. The apparatus according to claim 2, further comprising a control unit which controls the value-output circuit and the correction circuit.

5. The apparatus according to claim 4, wherein the control unit determines the number of the reference values which the value-output circuit outputs, based on a frame interval associated with imaging of the object.

6. The apparatus according to claim 5, wherein the control unit determines the number of the reference values which said value-output circuit outputs, based on a time period which is included in the frame interval associated with imaging of the object, and is unnecessary for imaging the object and the number of the lines of the plurality of pixel circuits.

7. The apparatus according to claim 6, wherein each of the plurality of pixel circuits comprises a resetting switch for resetting the photodiode unit, and wherein the control unit calculates the unnecessary time period by subtracting a time period for resetting in the resetting switch, a time period during which the X-ray is irradiated, a time period for the readout processing and a time period for the sample and hold, from the frame interval.

8. The apparatus according to claim 4, wherein the control unit controls the value-output circuit so that the value-output circuit outputs the predetermined reference value in advance before imaging the object.

9. The apparatus according to claim 1, wherein the value-output circuit comprises an A/D converter, and the value-output circuit outputs the measurement value which is A/D converted based on the analog signal or the reference value which is A/D converted based on the analog reference signal, and wherein the correction circuit comprises a D/A converter, and the correction circuit applies the correction value which is obtained from the predetermined reference value and the reference value and D/A converted, to an input of the A/D converter of the value-output circuit.

10. The apparatus according to claim 9, wherein said circuit comprises a plurality of the A/D converters, and wherein the correction circuit comprises a plurality of said D/A converters corresponding to respective ones of the A/D converters.

11. The apparatus according to claim 10, wherein the plurality of the pixel circuits are arranged over a plurality of semiconductor substrates, and wherein the plurality of the A/D converters are arranged corresponding to the plurality of the semiconductor substrates.

12. The apparatus according to claim 1, further comprising the X-ray tube.

13. The apparatus according to claim 1, wherein the value-output circuit comprises an amplifier and an A/D converter, and wherein the value-output circuit amplifies the analog signal and the analog reference signal, and wherein the value-output circuit outputs the measurement value which is A/D converted based on the amplified analog signal provided by the amplifier or based on the reference value which is A/D converted based on the amplified analog signal provided by the amplifier, and
   wherein the correction circuit comprises a D/A converter, and wherein the correction circuit applies the analog correction value signal which is obtained based on the reference value and the predetermined reference value and D/A converted, to an input of the amplifier.

14. The apparatus according to claim 13, wherein the value-output circuit comprises a plurality of the amplifiers and a plurality of the A/D converters, and
   wherein the correction circuit comprises a plurality of the D/A converters corresponding to respective ones of the plurality of A/D converters.

15. The apparatus according to claim 14, wherein the plurality of pixel circuits are arranged over a plurality of semiconductor substrates, and
   wherein the plurality of amplifiers and the plurality of A/D converters are arranged corresponding to respective ones of the plurality of semiconductor substrates.

16. An imaging apparatus for imaging an object based on X-rays that are irradiated from an X-ray tube and pass through the object, comprising:
- a plurality of pixel circuits which are arranged in a matrix and each of which outputs an analog signal corresponding to a received X-ray;
- a readout control circuit which controls a readout processing for reading out the analog signal for each line from the plurality of pixel circuits;
- a value-output circuit, comprising an A/D converter, which outputs a digital measurement value which is A/D converted based on the analog signal or a digital reference value which is A/D converted based on the analog reference signal; and
- a correction circuit which applies an analog correction value signal, for modifying the analog signal, derived from a predetermined digital reference value and a digital reference value which is outputted from the value-output circuit, corresponding to the analog reference signal during the period from a time at which the readout control circuit processes the readout processing for the plurality of pixel circuits for a certain line, to a time at which the readout control circuit processes the readout processing for the plurality of pixel circuits for a different next line, to an input of the A/D converter.

17. The apparatus according to claim 16, wherein each of the plurality of pixel circuits comprises a photodiode unit, a switch and a capacitor which sample and holds the analog signal corresponding to a voltage of the photodiode unit corresponding to the received X-ray.

18. The apparatus according to claim 17, wherein the value-output circuit outputs a plurality of the digital reference values during the time from when the readout control circuit processes the readout processing for the plurality of pixel circuits for a certain line to when the readout control circuit processes the readout processing for the plurality of pixel circuits for a next line, and wherein the correction circuit calculates the analog correction value signal based on a difference between an average value of the plurality of the digital reference values and the predetermined digital reference value.

19. The apparatus according to claim 17, further comprising a control unit which controls the value-output circuit and the correction circuit.

20. The apparatus according to claim 19, wherein the control unit determines the number of the digital reference values which the value-output circuit outputs, based on a frame interval associated with imaging of the object.

21. The apparatus according to claim 20, wherein the control unit determines the number of the digital reference values which the value-output circuit outputs, based on a time period which is included in the frame interval associated with imaging of the object, and is unnecessary for imaging the object, and the number of the lines of the plurality of the pixel circuits.

22. The apparatus according to claim 21, wherein each of the plurality of pixel circuits comprises a resetting switch for resetting the photodiode unit, and wherein the control unit calculates the unnecessary time period by subtracting a time period for resetting in the resetting switch, a time period during which the X-ray is irradiated, a time period for the readout processing and a time period for the sample and hold, from the frame interval.

23. The apparatus according to claim 19, wherein said control unit controls the value-output circuit so that the value-output circuit outputs the predetermined digital reference value in advance before imaging the object.

24. The apparatus according to claim 16, wherein the correction circuit comprises a D/A converter, which applies the analog correction value signal which is obtained from the predetermined digital reference value and the digital reference value and D/A converted, to an input of the A/D converter of the value-output circuit.

25. The apparatus according to claim 24, wherein the circuit comprises a plurality of the A/D converters, and wherein the correction circuit comprises a plurality of the D/A converters corresponding to respective ones of the A/D converters.

26. The apparatus according to claim 25, wherein the plurality of the pixel circuits are arranged over a plurality of semiconductor substrates, and wherein the plurality of the A/D converters are arranged corresponding to the plurality of the semiconductor substrates.

27. The apparatus according to claim 16, further comprising the X-ray tube.

28. The apparatus according to claim 16, wherein the value-output circuit further comprises an amplifier for amplifying the analog signal and the analog reference signal, and
- wherein the A/D converter outputs the digital measurement value which is A/D converted based on the amplified analog signal provided by the amplifier or based on the digital reference value which is A/D converted based on the amplified analog signal provided by the amplifier, and
- wherein the correction circuit comprises a D/A converter for applying the analog correction value signal which is obtained based on the digital reference value and the predetermined digital reference value and D/A converted, to an input of the amplifier.

29. The apparatus according to claim 28, wherein the value-output circuit comprises a plurality of the amplifiers and a plurality of the D/A converters, and
- wherein the correction circuit comprises a plurality of the D/A converters corresponding to respective ones of the plurality of A/D converters.

30. The apparatus according to claim 29, wherein the plurality of pixel circuits are arranged over a plurality of semiconductor substrates, and
- wherein the plurality of amplifiers and the plurality of A/D converters are arranged corresponding to respective ones of the plurality of semiconductor substrates.

* * * * *